United States Patent
Maurer et al.

(10) Patent No.: US 10,548,819 B2
(45) Date of Patent: Feb. 4, 2020

(54) DENTAL RETRACTION COMPOSITION, METHOD OF PRODUCTION AND USE THEREOF

(75) Inventors: Andreas R. Maurer, Langenneufnach (DE); Christoph Schulte, Windach (DE); Rüdiger Hampe, Landsberg (DE); Johannes M. Leykauff, Unterhausen (DE); Helmut Pauser, Diessen (DE)

(73) Assignee: 3M INNOVATIVE PROPERTIES COMPANY, St. Paul, MN (US)

( * ) Notice: Subject to any disclaimer, the term of this patent is extended or adjusted under 35 U.S.C. 154(b) by 208 days.

(21) Appl. No.: 13/375,038

(22) PCT Filed: May 24, 2010

(86) PCT No.: PCT/US2010/035901
§ 371 (c)(1),
(2), (4) Date: Nov. 29, 2011

(87) PCT Pub. No.: WO2010/138433
PCT Pub. Date: Dec. 2, 2010

(65) Prior Publication Data
US 2012/0077142 A1    Mar. 29, 2012

(30) Foreign Application Priority Data
May 29, 2009  (EP) .................................... 09161471

(51) Int. Cl.
*A61K 6/10* (2006.01)
(52) U.S. Cl.
CPC ..................... *A61K 6/10* (2013.01)
(58) Field of Classification Search
CPC ................. A61K 6/0011; A61K 6/10
(Continued)

(56) References Cited

U.S. PATENT DOCUMENTS

| 4,522,593 A | 6/1985 | Fischer |
| 4,871,311 A | 10/1989 | Hagne |

(Continued)

FOREIGN PATENT DOCUMENTS

| DE | 37 37 552 | 5/1989 |
| EP | 2 022 464 | 2/2009 |

(Continued)

OTHER PUBLICATIONS

PCT International Search Report for PCT Application No. PCT/US2010/035901 dated Jan. 10, 2010, 4 pages.

(Continued)

*Primary Examiner* — Cris L. Rodriguez
*Assistant Examiner* — Hao D Mai
(74) *Attorney, Agent, or Firm* — 3M Innovative Properties Compa

(57) ABSTRACT

The invention features a composition which can or is to be used in a dental retraction, the composition comprising liquid a liquid and a layer type 1:1 silicate mineral and a layer type 2:1 silicate mineral in a ratio from about 50/50 to 5/95 wt.-% with respect to each other. The invention also relates to a container containing the dental retraction composition and to a kit comprising parts A and B, wherein part A comprises the dental retraction composition and part B comprises at least one accessory selected from the group of applier, dental impression material, retraction cap(s), a container for storing and dispensing the composition and combinations thereof. The invention further features a process of dispensing a dental retraction composition, the process comprising the steps: providing a dental retraction composition contained in a container, placing the container in an applier, and using the applier for dispensing the dental retraction composition out of the container.

12 Claims, 5 Drawing Sheets

(58) Field of Classification Search
USPC ............ 433/80, 215, 136; 106/35; 424/434; 514/712
See application file for complete search history.

(56) References Cited

U.S. PATENT DOCUMENTS

| | | |
|---|---|---|
| 5,362,495 A | 11/1994 | Lesage |
| 5,865,803 A | 2/1999 | Major |
| 5,893,714 A | 4/1999 | Arnold et al. |
| 5,927,562 A | 7/1999 | Hammen et al. |
| 2004/0106086 A1 | 6/2004 | Dragan |
| 2005/0008583 A1 | 1/2005 | White |
| 2005/0069838 A1 | 3/2005 | Kollefrath et al. |
| 2005/0260543 A1 | 11/2005 | Dragan |
| 2005/0287494 A1 | 12/2005 | Yang et al. |
| 2008/0220050 A1* | 9/2008 | Chen et al. .................. 424/434 |
| 2008/0271636 A1* | 11/2008 | Kim ........................ A61K 6/10 106/35 |

FOREIGN PATENT DOCUMENTS

| | | |
|---|---|---|
| EP | 1 611 876 | 2/2012 |
| JP | 2006056833 | 3/2006 |
| WO | WO 2006/057535 | 6/2006 |

OTHER PUBLICATIONS

Partial European Search Report for European Application No. 09161471.9 performed Sep. 2, 2009, 4 pages.

Extended European Search Report for European Application No. 09161471.9 performed Sep. 2, 2009, 10 pages.

\* cited by examiner

DENTAL RETRACTION COMPOSITION, METHOD OF PRODUCTION AND USE THEREOF

CROSS REFERENCE TO RELATED APPLICATIONS

This application is a national stage filing under 35 U.S.C. 371 of PCT/US2010/035901, filed May 24, 2010, which claims priority to European Application No. 09161471.9, filed May 29, 2009, the disclosure of which is incorporated by reference in its/their entirety herein.

FIELD OF THE INVENTION

The invention relates to a dental retraction composition, a method for production and use thereof. The dental retraction composition comprises a liquid and a mixture of solids such as a silicate from the clay mineral group and a silicate from the Mica mineral group in a certain ratio. The composition can be used for retracting soft tissue from hard dental tissue.

BACKGROUND ART

For retracting gingiva from a prepared tooth a cord can be used. In this respect, a retraction cord is packed between gingival tissue and the margin of the prepared tooth (this region is also often called sulcus) using an appropriate dental instrument. To obtain sufficient vertical and horizontal retraction of gingival tissue, it is often necessary to pack several lengths of retraction cord into the sulcus in order to be able to make a detailed dental impression.

A description of the background in regard to retraction cords can be found e.g. in U.S. Pat. No. 4,522,593.

Generally, dental retraction cords are sometimes difficult to place into the gingival sulcus. The procedure can also be time consuming. It can also be cumbersome to remove the retraction cord prior to taking the impression. Coagulated blood may adhere to the cord and removing it may open the wound again which results in bleeding.

For a more convenient placement retraction pastes have been suggested.

A commercially available product to be used for retraction is sold under the name Expasyl™. However it is reviewed, that Expasyl™ is only effective under specific, limited conditions when the sulcus is flexible and of sufficient depth. The paste's thickness makes it difficult for some evaluators to express it into the sulcus. Moreover, according to the instruction of use, the viscosity of the composition might change when fluids like water, saliva or blood are absorbed.

Generally, removing non-hardening pastes completely out of the sulcus before taking the impression can be very time consuming and cumbersome. Usually, the paste is rinsed off using water-spray. However, sometimes paste residues are located deep in the sulcus and are thus difficult to remove. These residues might prevent the impression material from flowing into the sulcus area and may negatively influence the setting of the impression material which is subsequently applied. Moreover, after rinsing off the paste with water an additional drying step might be required before the impression can be taken. These removing and drying steps could cause bleeding of the tissue and might make an impression taking step more complicated.

Hardening materials are sometimes easier to remove. However, they are not very hydrophilic. This might cause problems with regard to flowability of the material into the gingival sulcus.

U.S. Pat. No. 5,362,495 refers to a method for widening the gingival sulcus without bleeding or oozing, comprising inserting within the gingival sulcus a material in the form of a biocompatible paste which is injectable for external use and having a plastic viscosity measured at 20° C. between about 13,000 and 30,000 Pa*s, wherein said material consisting of a material selected from the group of white clay, seaweed meal and mixtures thereof.

JP 2006056833 relates to a paste consisting of an astringent and filler containing clay mineral, torque, Mica, kaolin and/or montmorillonite.

US 2008/0220050 (Chen) relates to a composition for gingival retraction. The pasty composition contains water, clay, glass filler and astringent WO 2006/057535 (Kim) describes a composition comprising a certain amounts of kaolin clay, water, aluminium chloride hexahydrate, starch powder, silicone oil and coloring agent.

US 2005/008583 (White) describes a gingival retraction material comprising a carrying medium, a retraction medium and an anti-evaporating component. As an example the following material formula is given: kaolin powder (80 wt.-%), aluminium chloride (15 wt.-%), water/glycerine sufficient to produce a heavy plastic consistency, flavorings/colour as desired.

US 2005/0287494 (Yang) describes a gingival retraction material prepared by using fibrillated fibers to improve viscosity and combining taste-modifying agent, color agent and kaolin filler to form a paste-like structure having the viscosity ranging from $31.0*10^6$ cP to $71.0*10^6$ cP.

DESCRIPTION OF THE INVENTION

Thus, there is still a need for an improved dental retraction composition.

Ideally, a composition is desired, which can be applied into a patient's sulcus using a commercially available applier.

Moreover, it would be advantageous, if the material can easily be rinsed from the sulcus.

Additionally, according to a preferred embodiment, the material should ideally have a sufficient storage modulus.

In one embodiment the present invention features a dental composition, in particular a dental retraction composition or a composition which can or is to be used in a retraction procedure or for retracting soft dental tissue from hard dental tissue, the composition comprising a liquid and a layer type 1:1 silicate mineral and a layer type 2:1 silicate mineral in a ratio from about 50/50 to 5/95 wt.-% with respect to each other.

In another embodiment, the invention relates to a container containing the dental retraction composition as described in the text of the present invention.

In a further embodiment, the invention is directed to a kit comprising parts A and B, wherein part A comprises the dental retraction composition of the present invention and part B comprises at least one accessory selected from the group of applier, dental impression material, retraction cap(s), a container for storing and dispensing the composition and combinations thereof.

The invention also relates to a process of manufacturing a dental retraction composition as described in the text of the present invention, the process comprising a mixing step.

The invention also refers to a process for producing a means for retracting soft dental tissue from hard dental tissue, wherein the process comprises the step of filling a composition as described in the text of the invention into a container comprising a cannula and a reservoir.

The invention further features a process of dispensing a dental retraction composition, the process comprising the steps:
providing a dental retraction composition as described in the text of the invention contained in a container,
placing the container in an applier, and
using the applier for dispensing the dental retraction composition out of the container.

Moreover, the invention relates to the use of the dental retraction composition as described in the text of the present invention for retracting soft dental tissue from hard dental tissue.

A further aspect of the invention is directed to the use of a layer type 2:1 silicate mineral for producing a dental retraction composition, the dental retraction composition comprising in addition a liquid and a layer type 1:1 silicate mineral.

Definitions

Unless otherwise specified, within the context of the text of the invention, the following terms have the following meanings.

A "composition" is understood to be a mixture or combination of two or more components.

A "dental composition" is any composition which can be used in the dental or orthodontic field. In this respect the composition should be not detrimental to the patient's health and thus free of hazardous and toxic components being able to migrate out of the composition.

A "dental retraction composition" is a composition enabling the practitioner to retract soft dental tissue (e.g. gingiva) away from hard dental tissue (e.g. tooth) before or during an impression of the tooth structure is made.

A "tooth structure" is any tooth structure, prepared or ready for preparation by the dentist. It can be a single tooth or two or more teeth. A tooth structure is also referred to as hard dental tissue in contrast to soft dental tissue (e.g. gingiva).

A "dental impression material" is a material used for making impressions of the tooth structure including the gingiva. A dental impression material is usually applied on a dental impression tray. A dental impression material can be based on different chemical substances and crosslink by various chemical reactions (including addition curing and condensation curing materials). Typical examples include silicone based impression materials (e.g. VPS materials) and polyether based impression materials and mixtures of those.

A "liquid" is any solvent or liquid which is able to at least partially disperse, dissolve or suspend the components being present in the inventive composition at ambient conditions (e.g. 23° C.).

A "paste" is a substance that behaves as a solid until a sufficiently large load or stress is applied, at which point it flows like a fluid. Pastes typically consist of a suspension of granular material in a background fluid. The individual grains are jammed together like sand on a beach, forming a disordered, glassy or amorphous structure, and giving pastes their solid-like character. Pastes can be classified by their viscosity or their consistency comparable to dental impression material (cf. ISO 4823).

A "haemostatic agent" is an agent which is able to reduce bleeding to a certain amount and/or causes blood to coagulate. Haemostatic agents are also sometimes referred to as astringents.

A "particle" means a substance being a solid having a shape which can be geometrically determined. The shape can be regular or irregular. Particles can typically be analysed with respect to e.g. grain size and grain size distribution.

If desired, the particle size can be measured using a Cilas 1064 LD Nass (Cilas, France) light scattering instrument. The Cilas 1064 uses an integrated optical system to cover the range from 0.04 to 500 μm. The mixtures to be analyzed are added to the test chamber filled with water. Ultrasound is applied for about 60 s in order not to alter the particle size distributions and to avoid agglomeration. The raw data is processed with the instrument software using the Fraunhofer approximation, frequently used techniques known to the expert in the art.

"Phyllosilicates" are silicates forming sheets of silicate tetrahedra with $Si_2O_5$. Phyllosilicates can be further divided in sub-groups, e.g. according to the number of sheets or layers arranged with each other.

Within the meaning of the present invention, phyllosilicates are divided in the following subgroups: silicate minerals of the 2:1 layer type group and silicate minerals of the 1:1 layer type group.

With respect to this classification a more detailed description can be found in Ullmanns Encyclopedia of Industrial Chemistry (Wiley-VCH), 2005, Silicates; especially table 4.

According to this reference, the clay minerals belong to the group of phyllosilicates and can be characterized by the number of layers linked or arranged with each other. This classification is also used in the present invention.

E.g., in kaolinite, having the ideal formula $Al_2[Si_2O_5(OH)_4]$), two single layers are linked or arranged with each other.

E.g. in muscovite, having the ideal formula $KAl_2(AlSi_3O_{10})(OH)_2$ and belonging to the Mica type group of minerals, three layers are linked or arranged with each other.

The terms "crosslinking", "hardening", "setting", "curing" or "curable" are used interchangeable, all referring to the formation of material with a higher molecular weight and/or to the formation of a material having a higher viscosity, by creating a network due to chemical and/or physical interaction.

A "hardening-", "curing-" or "setting-reaction" is a reaction, wherein physical properties such as viscosity, and tensile strength of a composition change over the time due to a chemical or physical reaction between the individual components.

A composition or solution is "essentially or substantially free of" a certain component, if the composition does not contain said component as an essential feature. Thus, said component is not wilfully added to the composition either as such or in combination with other components or ingredient of other components. A composition being essentially free of a certain component usually contains the component in an amount of less than about 1 wt.-% or less than about 0.1 wt.-% or less than about 0.01 wt.-% with respect to the whole composition. Ideally the composition does not contain the said component at all. However, sometimes the presence of a small amount of the said component is not avoidable e.g. due to impurities.

"Ambient conditions" mean the conditions which the inventive solution is usually subjected to during storage and handling. Ambient conditions may, for example, be a pressure of about 900 to about 1100 mbar, a temperature of about 0 to about 50° C. and a relative humidity of about 10 to about 100%. In the laboratory ambient conditions are adjusted to about 23° C. and about 1013 mbar.

If not indicated otherwise "molecular weight" always means Mw (weight average of the molecular weight) and can be determined for the individual classes of polymers by gel permeation chromatography (GPC) against a standard of defined molecular weight. Suitable measurement methods are known to the person skilled in the art.

As used herein, "a", "an", "the", "at least one" and "one or more" are used interchangeably. The terms "comprises" or "contains" and variations thereof do not have a limiting meaning where these terms appear in the description and claims. Also herein, the recitations of numerical ranges by endpoints include all numbers subsumed within that range (e.g., 1 to 5 includes 1, 1.5, 2, 2.75, 3, 3.80, 4, 5, etc.).

If not indicated otherwise, wt.-% always refers to the weight of the whole composition.

DETAILED DESCRIPTION OF THE INVENTION

Figure 1:
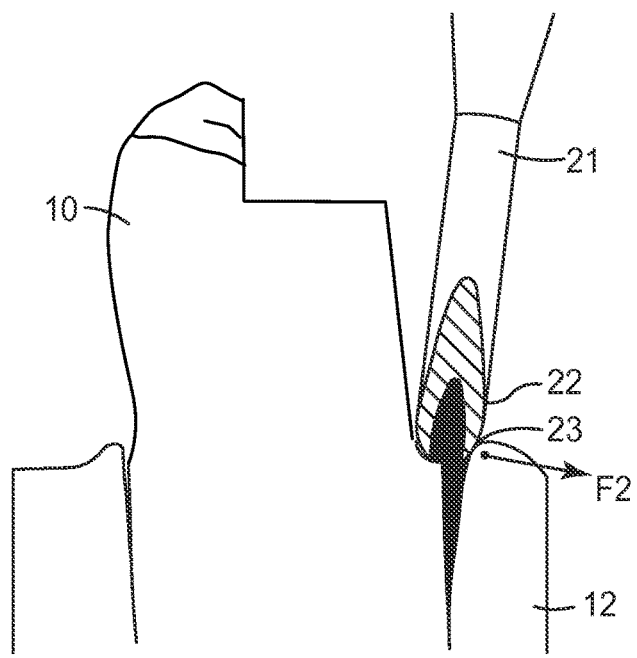
FIG. 1 is a view of a tooth prepared for restoration and a cannula of a container which can be used for storing and dispensing of a dental retraction composition.

It has been found that the inventive dental retraction composition typically shows a couple advantageous features.

The composition typically has a sufficient good storage modulus (e.g. at least about 2000 kPa).

A dental retraction paste, which does not have a sufficient storage modulus, is often difficult to apply into the sulcus. The tooth surrounding tissue forming the sulcus and having certain elasticity often repels the applied composition. That is, if the storage modulus is too low, the paste will be partly squeezed out of the sulcus which may result in an inefficient retraction. By applying to and/or packing the dental retraction composition e.g. with the aid of a nozzle or cannula, into the sulcus, a sufficient mechanical retraction of the gingiva can be achieved.

After application of the composition to the sulcus, the inventive composition can be removed or rinsed out within a short period of time.

This may be caused by the smooth surface of the dental retraction composition. A smooth surface may not only facilitate an easy removal out of the sulcus (e.g. within about 10 s using a water-air beam) but also may further prevent sticking of the composition to coagulated blood which may be present in the sulcus. Sticking often may cause an undesired wound opening and bleeding upon removal of the retraction composition.

This characteristic can be advantageous in several ways. E.g., the dental practitioner saves working time, the treatment time for the patient is reduced and the quality of the impression to be taken afterwards is often improved, as well. In contrast to that, residues of a dental retraction composition remaining in the sulcus can cause infections and also may influence the hardening reaction of a curable dental impression material, thus leading to a less accurate dental impression.

Moreover, it was found that, if the composition is stored in a specific container with a cannula or nozzle having certain dimensions, the composition can be applied to the sulcus using a commercially available dispensing device with acceptable extrusion forces (e.g. less than or equal to about 150 N).

The inventive dental retraction composition comprises a liquid and a layer type 1:1 silicate mineral and a layer type 2:1 silicate mineral in a certain ratio with respect to each other.

Liquids which can be used include polar and non-polar liquids and mixtures thereof.

Specific examples include water, alcohols (e.g. ethanol, n- and iso-propanol, ketons (e.g. acetone), glycerine (e.g. ethoxylated glycerin), glycols (e.g. ethylene glycol, propylene glycol) and silicon oils. The content of liquid in the composition is not particularly limited, unless the desired advantages cannot be obtained.

Liquid is typically present in an amount of at least about 10 wt.-% or at least about 15 wt.-% or at least about 20 wt.-% with respect to the whole composition.

Liquid can be present in an amount up to about 35 wt.-% or up to about 30 wt.-% or up to about 25 wt.-% with respect to the whole composition.

Typical wt.-% ranges for liquid being present in the composition include from about 10.-% to about 35 wt.-% or from about 15 wt.-% to about 30 wt.-%.

If the content of liquid in the composition is too low, the viscosity of the composition typically increases having the result that the extrusion force needed for dispensing the composition from a container might increase as well.

If the content of liquid in the composition is too high, the viscosity of the composition typically decreases having the result that the storage modulus might be insufficient and may hamper the application of the composition into the sulcus.

Liquids suitable for preparing the dental retraction composition of the invention include those, which are able to form a paste or gel with the other components present.

Typically, the liquid contains a high amount of water (e.g. above about 50 or above about 70 or above about 90 vol.-%) or consists of water only. Mixtures with alcohols (e.g. ethanol) or ketons (e.g. acetone) or silicon oils can be used as well.

With respect to certain formulations it has been found that given a specific ratio of layer type 1:1 silicate mineral towards layer type 2:1 silicate mineral, the water content does typically not influence the rinsing time. However, with increasing water content a decrease in the storage modulus and extrusion force has been found.

The inventive dental retraction composition comprises the liquid in an amount sufficient to form a viscous paste with the other components being present in the composition.

It was found that using a combination of water and an oil (especially a silicone oil) can be beneficial, especially if a good balance between storage modulus and rinsing time should be achieved.

Useful oils include silicone oil (like polydimethylsiloxane trimethylsiloxy terminated) or any other polyalkylsiloxanes.

The ratio of water to (silicone) oil is typically within a range from about 1:1 to about 1000:1 or from about 20:1 to about 250:1 (with respect to weight of the components).

If the ratio is outside these ranges, a sufficient balance between storage modulus and rinsing time is sometimes difficult to achieve.

Phyllosilicates from the layer type 1:1 silicate mineral which can be used include kaolinite, lizardite, halloysite and mixtures or combinations thereof, wherein kaolinite is preferred.

The particle size of the layer type 1:1 silicate mineral is not particularly limited, unless the resulting paste gets to inhomogeneous or shows an unesthetic look.

The mean particle size is typically in a range between about 0.01 and about 100 μm or between about 0.1 and about 50 μm or between about 1 and about 25 μm.

The content of the layer type 1:1 silicate mineral in the composition is not particularly limited, unless the desired advantages cannot be obtained.

The layer type 1:1 silicate mineral is typically present in an amount of at least about 1 wt.-% or at least about 2 wt.-% or at least about 3 wt.-% with respect to the whole composition.

The layer type 1:1 silicate mineral can be present in an amount up to about 40 wt.-% or up to about 35 wt.-% or up to about 30 wt.-% with respect to the whole composition.

Typical ranges for the layer type 1:1 silicate mineral being present in the composition include from about 1 wt.-% to about 40 wt.-% or from about 2 wt.-% to about 35 wt.-%.

If the content of the layer type 1:1 silicate mineral in the composition is too low, the storage modulus might decrease to a not sufficient level.

If the content of the layer type 1:1 silicate mineral in the composition is too high, the extrusion force might increase to a not desired level. Also the rinsing time might be negatively affected.

Phyllosilicates from the layer type 2:1 silicate minerals which can be used include talc-pyrophyllite type minerals, smectite type minerals, vermiculite type minerals, illites type minerals, mica type minerals and mixtures and combinations thereof.

Specific examples include talc, willemseite, pyrophyllite, stevensite, saponite (from the talc-pyrophyllite type group of minerals), stevensite, sponite, sauconite, hectorite, montmorillonite, beidellite, nontronite, volkonskite (from the smectite type group of minerals), phlogopite, biotite, lepidolite, muscovite, illite, glauconite, celadonite (from the mica type group of minerals).

Layer type 2:1 silicate minerals which do not significantly swell when combined with water or show essentially no swelling at all, were found to be especially beneficial. Those silicate minerals include muscovite and phlogopite. For example, the silicate mineral bentonite was found to be not particularly useful as it shows certain undesirable water solubility.

The particle size of the layer type 2:1 silicate mineral is not particularly limited, unless the resulting composition gets too inhomogeneous.

The mean particle size is typically between about 0.01 and about 100 μm or between about 0.1 and about 50 μm or between about 1 and about 25 μm.

The content of the layer type 2:1 silicate mineral in the composition is not particularly limited, unless the desired advantages cannot be obtained.

The layer type 2:1 silicate mineral is typically present in an amount of at least about 25 wt.-% or at least about 30 wt.-% or at least about 35 wt.-% with respect to the whole composition.

The layer type 2:1 silicate mineral can be present in an amount up to about 70 wt.-% or up to about 65 wt.-% or up to about 60 wt.-% with respect to the whole composition.

Typical wt.-% ranges for the layer type 2:1 silicate mineral being present in the composition include from about 25 wt.-% to about 70 wt.-% or from about 30 wt.-% to about 65 wt.-%.

If the content of the layer type 2:1 silicate mineral in the composition is too low, the extrusion force might increase to a level, which is not desired. The rinsing time needed for removing the composition from the sulcus might increase as well.

If the content of the layer type 2:1 silicate mineral in the composition is too high, the storage modulus might decrease to a level at which no sufficient retraction can be achieved.

The layer type 1:1 silicate mineral and the layer type 2:1 silicate mineral are typically present in the dental retraction composition in a certain weight ratio with respect to each other.

This weight ratio includes a range from about 50/50 to about 5/95 or from about 30/70 to about 10/90.

That is, the content of the layer type 1:1 silicate mineral and the content of the layer type 2:1 silicate mineral in the dental retraction composition can be about equal.

It is, however, also within the scope of the invention that the layer type 2:1 silicate mineral is present in excess compared to the layer type 1:1 silicate mineral.

If the ratio is outside the above mentioned ranges, the resulting dental retraction composition might not sufficiently achieve the preferred combination features, like low extrusion force combined with high storage modulus and short rinsing time.

Figure 4:
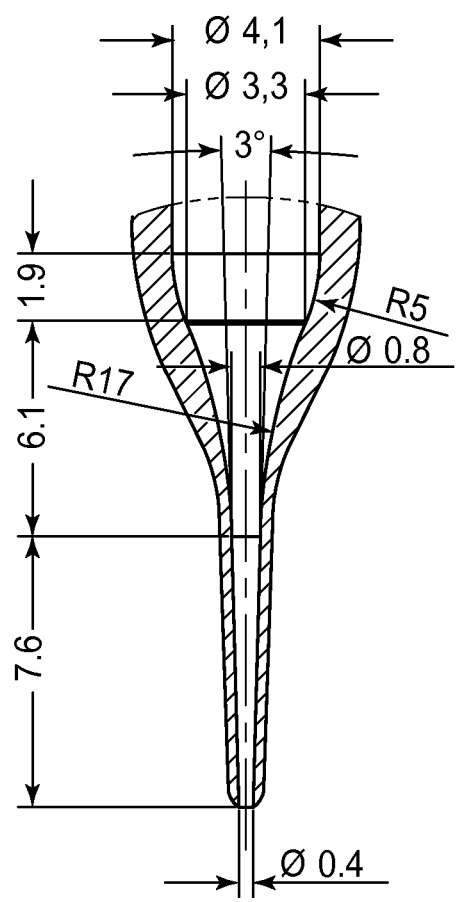
FIG. 4 shows the front end (cannula) of the container which was used for measuring the extrusion force.
Figure 5:
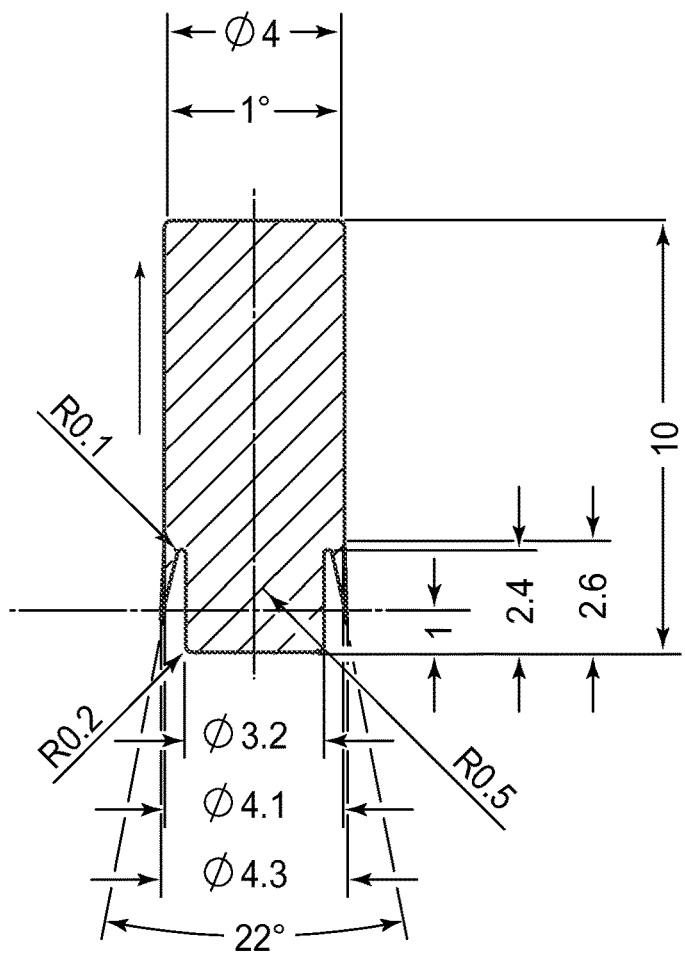
FIG. 5 shows the piston inserted in the container which was used for measuring the extrusion force.
Figure 6:
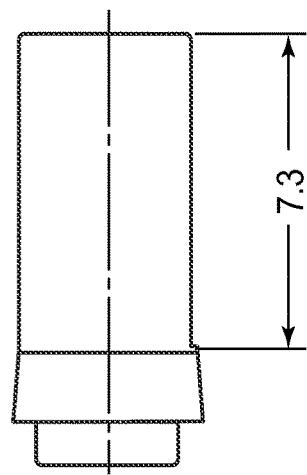
FIG. 6 shows the piston inserted in the container which was used for measuring the extrusion force.

The invention is also directed to a dental retraction composition comprising a liquid and a solid in a ratio that at least one, two or even all of the following characteristics are met:

Storage modulus: at least about 2000 kPa or at least about 2500 kPa or at least about 3000 kPa Extrusion force: less than or equal to about 150 N or below about 140 N or below about 130 N, e.g. if the dental retraction composition is dispensed from a container having a cannula with the dimension shown in FIG. 4 using a piston as shown in FIGS. 5 and 6.

Rinsing time: less than or equal to about 11 or less than or equal to about 10 s.

It was found that a composition showing a good balance between sufficient storage modulus and adequate rinsing time is beneficial for the practitioner.

If desired, the storage modulus can be determined as described in the example section below.

A dental retraction composition having a storage modulus below about 2000 kPa often does not have enough structural performance. That is, the composition cannot easily be placed in the sulcus and if the practitioner succeeds in placing the composition in the sulcus, the composition typically does not remain sufficiently long in the sulcus. Due to the resilience of the surrounding tissue, the composition is often squeezed out of the sulcus.

If desired, the rinsing time can be determined as described in the example section below.

As explained above, a short rinsing time may have several advantages. The shorter the time needed for removing the composition from the sulcus, the better it typically is due to the limited timeframe for taking the subsequent impression of the prepared tooth structure.

The same is true for the extrusion force needed to dispense the composition from a container or compule. The lower the value of the extrusion force typically is, the easier and more convenient the composition can be applied.

If desired, the extrusion force can be determined as described in the example section below.

The inventive dental retraction composition can also comprise one or more astringents (sometimes also referred to as haemostatic agent).

There is no need for an astringent to be present. However, if an astringent is present, it is present in an amount which typically supports the intended purpose, that is, to facilitate the whole retraction procedure.

Astringent(s) that may be useful in assisting haemostasis include, but are not limited to oxides, chloride or sulphate salts of ferrum (e.g. ferric sulfate, ferric subsulfate, ferric chloride), aluminium (e.g. potassium aluminum sulfate, aluminum ammonium sulfate, aluminum sulfate, aluminum chlorohydrate, aluminum acetate) and zinc, polyphenols, ellag acid, permanganates (e.g. potassium permanganate), potassium ferrate (IV), silver nitrate and hydrogen peroxide, epinephrine and mixtures thereof. One preferred class of haemostatics include aluminum compounds.

The astringent can be present in an amount of at least about 0.01 wt.-% or at least about 5 wt.-% or at least about 10 wt.-% with respect to the whole composition.

The astringent can be present in an amount up to about 30 wt.-% or up to about 25 wt.-% or up to about 20 wt.-% with respect to the whole composition.

If an astringent agent is present, it is typically present in an amount of about 0.01 wt.-% to about 30 wt.-% or in an amount of about 5 wt.-% to about 25 wt.-% or in an amount of about 10 wt.-% to about 20 wt.-% with respect to the weight of the whole composition.

If the content of the astringent in the composition is too low, a sufficient haemostasis can typically not be achieved.

If, on the other hand, the content of the astringent in the composition is too high, the treated tissue might be damaged. Moreover, the astringent agent might interfere with the other components present in the composition and might cause undesired coagulation or clogging.

The inventive dental retraction composition can also comprise one or more additives.

Additives, which can be present in the composition, include colourants, pharmaceutical drugs, anti-microbial agents, anti-evaporation agents, rheology modifiers, flavouring agents, preserving agents, surfactants, pH buffering agent and mixtures and combinations thereof.

There is no need for additives to be present however if one or more additives are present, they are typically present in an amount which supports the intended purpose, that is, to facilitate the whole retraction procedure.

Additive(s) can be present in an amount of at least about 0.0001 wt.-% or at least about 0.1 wt.-% or at least about 1 wt.-% with respect to the whole composition.

According to one embodiment, the dental retraction composition has a colour which may allow an easy detection in a patient's mouth (especially compared to oral tissue and/or tooth substance) and control whether after the treatment all residues of the retraction device have been removed from the sulcus. E.g., a blue, green or yellow colour may be suitable. However, in view of some new impression techniques like e.g. digital scanning, other colours might be preferred. Some techniques prefer colours that are less visible for the scanning instrument e.g. red or white. Colouring of the retraction device can be achieved by incorporating colorants or pigments (organic and inorganic) into the composition.

Examples of colourants which can be used include chinoline yellow dye (sicovit), chromophtalblue A3R, red iron oxide 3395, Bayferrox 920 Z Yellow, Neazopon Blue 807 (copper phthalocyanine-based dye), Helio Fast Yellow ER, Brilliant Blue FCF, Fast Green FCF and/or Orange Yellow S. Pigments or dyes which are stable under acidic conditions are preferred.

According to another embodiment, the dental retraction composition may also comprise an anti-evaporating agent. Anti-evaporating agents, which can be used, include polyethylene glycols or polypropylene glycols or mixed poly glycols (e.g. having a molecular weight Mw in the range of about 200 g/mol to about 10,000 g/mol or in a range of about 500 g/mol to about 3,000 g/mol). If an anti-evaporating agent is present, it is typically present in an amount of about 0.01 wt.-% to about 30 wt.-% or in an amount of about 1 wt.-% to about 10 wt.-% with respect to the whole composition.

According to a further embodiment, pharmaceutical drugs can be added. Pharmaceutical drugs might contribute or enhance a haemostatic effect, e.g. caused by the addition of an astringent. Pharmaceutical drugs which can be added include adrenaline, epinephrine, propylhexidrin, adrenochrom-monose Micarbazone propylgallat, tranexamic acid, etamsylate, batroxobin, thrombin, fibrin dressings.

In another embodiment of the invention, the dental retraction composition may comprise one or more surfactants. Typical surfactants, which can be used, include anionic, cationic or non-ionic surfactants.

There is no need for a surfactant to be present at all. However, if a surfactant is present, it is typically present in an amount of up to about 2 wt.-% or up to about 1 wt.-% or up to about 0.05 wt.-%, with respect to the whole composition.

In another embodiment of the invention, the dental retraction composition may comprise a pH buffering agent. The addition of a pH buffering agent might facilitate adjusting the pH value, in particular making the retraction composition less acidic. Typical pH buffering agents, which can be used, include but are not limited to carbonates and phosphates (e.g. alkali carbonate or alkali bicarbonate).

There is no need for a pH buffering agent to be present at all. However, if a pH buffering agent is present, it is typically present in an amount of up to about 10 wt.-% or up to about 2 wt.-% of up to about 0.5 wt.-%, with respect to the whole composition.

In another embodiment of the invention, the dental retraction composition may comprise a flavorant or mixtures of flavorants to improve the taste and/or smell of the composition. Typical flavorants, which can be used, include but are not limited to Isoamylacetate (banana), Benzaldehyde (bitter almond). Cinnamic aldehyde (Cinnamon), Ethylpropionate (fruity), Methyl anthranilate (Grape), mints (e.g. peppermints), Limonene (e.g. Orange), Allylhexanoate (pineapple), Ethylmaltol (candy), Ethylvanillin (Vanilla), Methylsalicylate (Wintergreen).

There is no need for a flavorant to be present at all. However, if a flavorant agent is present, it is typically present in an amount of up to about 3 wt.-% or up to about 0.1 wt.-% of up to about 0.01 wt.-%, with respect to the whole composition.

A typical inventive dental retraction composition may have the following formulation:
liquid in an amount from about 10 wt.-% to about 35 wt.-% or from about 15 wt.-% to about 30 wt.-%, layer type 1:1 silicate mineral in an amount from about 1 wt.-% to about 40 wt.-% or from about 2 wt.-% to about 35 wt. % or from about 3 wt.-% to about 30 wt.-%, the layer type 2:1 silicate mineral in an amount from about 25 wt.-% to about 70 wt.-% or from about 30 wt.-% to about 65 wt.-% or from about 35 wt.-% to about 60 wt.-%, astringent in an amount from about 0.01 wt.-% to about 30 wt.-% or from about 5 wt.-% to about 25 wt.-% or from about 10 wt.-% to about 20 wt.-%, additives in an amount from about 0.0001 wt.-% to about 30 wt.-% or from about 0.1 wt.-% to about 20 wt.-% or from about 0.5 wt.-% to about 10 wt.-% or from about 1 to about 5 wt.-%.

The invention is also directed to a dental retraction composition as described in the text of the present invention which is contained in a container.

The composition of the invention is preferably provided to the practitioner under hygienic conditions. One possibility to achieve this includes packing or storing the retraction composition in a sealed container such as a capsules, cartridge or foil bag under hygienic conditions.

Thus, the inventive dental retraction composition is typically stored in a container or storage device. Usually, the container has a front end and a rear end, a piston movable in the container and a nozzle or cannula for delivering or dispensing the composition located in the container. The container has usually only one compartment or reservoir.

The container typically has a volume in the range from about 0.1 to about 1 ml. This is the volume typically needed for a single dental retraction procedure. The container is typically used only once (e.g. disposable packing).

The composition can be dispensed out of the container by moving the piston in the direction of the nozzle. The piston can be moved either manually or with the aid of an application device or applier designed to receive the container (e.g. an application device having the design of a caulk gun).

Examples of containers which can be used include compules, syringes and screw tubes. Containers of this kind are exemplified in more detail e.g. in U.S. Pat. Nos. 5,927,562, 5,893,714 or 5,865,803, the content of which in regard to the description of containers is herewith incorporated by reference.

It can be advantageous, if a container is used comprising a nozzle having a shape and size, which allows an easy and safe application of the dental retraction composition in the sulcus.

Useful containers typically have a hollow body (typically of cylindrical or conical shape) with a front end and a rear end in which the dental retraction composition is stored. The rear end is typically sealed with a piston, being movable in the hollow body. At the front end of the hollow body, there is typically a nozzle having a size and shape which enables the practitioner to dispense the inventive dental retraction composition into the sulcus of a patient. The smaller the diameter of the nozzle is, the easier the nozzle can be placed into the sulcus. However, a small diameter of the nozzle may result in an increase of the extrusion force needed to dispense the dental retraction composition out of the device. Thus, not all cannula sizes and diameters are suitable. A device with a nozzle or cannula having an external diameter in the range from about 0.6 mm to about 1.3 mm and an internal diameter in the range from about 0.2 mm to about 0.9 mm has been found to be particular useful.

However, other shapes and diameters can be used as well, if the intended effect (i.e. widening of the sulcus) can be achieved.

It has been found that especially the combination of a certain container containing the inventive dental retraction composition is particularly suited to address the object of the present invention. Such a container is described in more detail in application no. EP 08158033 filed on Jun. 11, 2008, the content of which is herewith incorporated by reference and considered part of this invention.

If this particular combination is used, the dental retraction composition can easily be dispensed into the sulcus of a tooth and the desired retraction achieved.

The container which can advantageously be used for storing and dispensing the inventive retraction composition comprises a cannula that has a free end which comprises an opening for dispensing the dental composition.

Such a container facilitates the application of the composition into the sulcus in that it provides a mechanical means which allows an easy widening of the sulcus with the aid of the cannula. Once the sulcus has been widened, the inventive composition can easily be applied and due to its sufficient storage modulus may help stabilizing the widened sulcus.

In one embodiment the free end and the opening are shaped so that the opening can be positioned to the entry of the gingival sulcus, with an outer lateral surface of the free end touching the tooth and the gingiva. The free end is further preferably shaped so that the gingiva is laterally displaced, for example predominantly laterally displaced, from the tooth as the cannula is further moved with the opening toward the inside of the gingival sulcus. Thus, the cannula preferably allows for injecting the dental retraction composition in a pre-opened gingival sulcus which may help to reliably fill the gingival sulcus with the dental retraction composition.

In another embodiment the free end has an outer lateral surface which extends between a first outer diameter D1 and a second outer diameter D2. Preferably the first outer diameter D1 is located adjacent the front of the free end, or at the front most end. The second outer diameter D2 is preferably located at a distance L2 further to the rear from the first outer diameter D1. D2 is preferably greater than D1. This preferably enables the device to displace the gingiva laterally away from the tooth, and preferably thereby enables the device to widen the gingival sulcus as the free end is moved farther into the gingival sulcus.

The term "diameter" may be generally interpreted as "cross-sectional dimension", for cases in which a non-circular cross-section is provided.

The diameter D1 may be between about 0.2 mm and about 1 mm, in particular between about 0.3 mm and about 0.7 mm, or between about 0.3 mm and about 0.8 mm, in more particular D1 may be within a range of about 0.4 mm to 0.6 mm. The diameter D1 is preferably about 0.4 mm. A relatively small dimension of the outer diameter D1 preferably allows, for example, the front of the free end to be inserted in the entry of the gingival sulcus relatively easily. Further such dimensions may help to reduce the risk of injuries of the gingival tissue during insertion of the front of the free end in the entry of the gingival sulcus, because it fits between the tooth and the gingiva rather than pressing on the gingiva itself.

The diameter D2 may be between about 0.7 mm and about 1.4 mm, in particular between about 0.7 mm and 1.3 mm, in more particular the diameter D2 may be between about 0.9 and 1.3 mm. Preferably the diameter D2 is about 1.1 mm. Such dimensions may for example provide the free end of the cannula with a sufficient stiffness, and on the other hand may still provide good interproximal access for the free end.

Therefore, the device described in the text of the invention may be suitable to inject a dental retraction composition in the gingival sulcus all around a tooth in a controlled manner, and not only at distal or lingual portions of the gingival sulcus.

The length L2 of the free end may be between about 0.3 mm and about 2 mm, in particular between about 0.3 mm and about 1 mm, and preferably about 0.5 mm.

In another embodiment the first outer diameter D1 is located adjacent the opening. The first outer diameter D1 may also be formed by the opening. The opening may have a first inner diameter P1 which is between about 0.2 mm and 1 mm, however the opening may further have a first inner diameter P1 which is between about 0.3 mm and about 0.7 mm. In particular P1 may be within a range of about 0.4 mm to 0.6 mm, and preferably about 0.4 mm. P1 may be smaller than D1, but is preferably about equal to D1. In latter case P1 and D1 both refer to the diameter of the opening. In particular, the inner diameter P1 may provide for the flow rate of a high viscosity dental composition to be controlled relatively precisely as the composition is injected into the gingival sulcus.

In another embodiment the lateral outer surface of the free end tapers from the second outer diameter D2 toward the first outer diameter D1. Thus, the taper preferably tapers in a direction from D2 toward D1. Furthermore the taper preferably tapers based on a curve having a relatively constant radius R. The Radius R may be greater than ½ of D2. For example, the shape of the free end may resemble a nose cone, a convex cone, or a radial cone. A curve resembling a radius greater than ½ of D2 may provide for a relatively low force required to insert the free end of the cannula in the entry of the gingival sulcus. Relative to a linear cone such convex or radial cone may further provide for a less blunt front-most end, which may reduce the risk of injuring the gingiva when inserted into the gingival sulcus.

The cannula of the container described in the text of the invention may have a length L1 between the first outer diameter D1 and a third outer diameter D3. The cannula may have a shaft portion extending between the second outer diameter D2 and the third outer diameter D3. The shaft portion and the free end may be located adjacent to each other, and together extend along the length L1. The third outer diameter D3 may be between about 0.7 mm and about 2 mm, in particular between about 1.3 mm to about 1.9 mm, and preferably about 1.7 mm. D3 is preferably greater than D2, but may also be about equal to D2. Thus, the shaft portion may be generally cylindrical or conical. Preferably the shaft portion smoothly transitions to the free end. The length L1 may be between about 6 mm and about 18 mm, in particular between about 8 mm and about 10 mm, and preferably about 9 mm. Such dimensions preferably allow the cannula to access areas that are accessible only through narrow spaces in a patient's mouth, for example a gingival sulcus between two teeth. This may also help in injecting a dental composition around substantially the entire perimeter of a tooth.

In one embodiment the cannula has a marking. The marking preferably is usable as reference with regard to a certain (for example a preferred) penetration depth of the cannula in the gingival sulcus. The marking may help a user to observe and/or to assess the depth to which the cannula is inserted in the gingival sulcus during a treatment of a patient. Therefore, a user may control the penetration depth of the cannula relatively precisely and thereby may achieve an effective gingival retraction. On the other hand this may help to avoid damage to the gingival tissue which may result from too deep penetration of the cannula in the gingival sulcus. The marking may be a notch, a rim, a step, or a (printed) line, for example. The marking may extend partly or entirely circumferentially around the cannula. The marking may further be formed by a transition between colors of outside surfaces of the cannula. For example, the front end of the cannula may have a certain first outside color, and an adjacent rear portion of the cannula may have a certain second outside color, wherein the first and second colors are different. The marking may also be formed by a transition between areas of different transparency or translucency. Preferably the marking is formed by a transition between surface structures of outside surfaces of the cannula. For example, the front end of the cannula may have a generally even or glossy outside surface, and an adjacent rear portion of the cannula may have a more rough or matte outside surface. The marking may also be a scale marking different penetration depths.

In one embodiment the container comprises a cartridge having a chamber for receiving and storing the dental retraction composition. The container is preferably adapted for comprising a piston, or may comprise a piston. The container is preferably adapted for dispensing the dental retraction composition through the cannula. The cartridge may extend along a longitudinal axis, and the piston may be movable along the longitudinal axis for urging the dental retraction composition towards the cannula. The chamber may, for example open into a nozzle to which the cannula can be adapted. Alternatively the chamber may open into the cannula. The cannula may be fixedly attached to the cartridge. For example, the cannula and the cartridge may be co-injection molded. In another embodiment the cannula and the cartridge are made from different plastic materials. For example the cartridge may be made of a more rigid plastic material than the cannula. Therefore, the cartridge may provide sufficient stability for extruding the composition, and the cannula may be sufficiently soft to reduce the risk of injuries of the gingiva while in use.

In another embodiment the cannula may extend along a longitudinal axis which is inclined relative to the longitudinal axis of the cartridge by an angle of between about 30 degrees and about 60 degrees, preferably by about 45 degrees. The cannula may also extend along a curve, and a central axis through the opening of the cannula may be inclined relative to the longitudinal axis of the cartridge by an angle of between about 30 degrees and about 60 degrees, preferably by about 45 degrees.

In another embodiment the cannula comprises a passageway between the opening with the first inner diameter P1 and an inlet with a second inner diameter P2, wherein P2 is between about 0.3 and 1.0 mm. P2 is preferably greater than or equal to P1. Thus the passageway may taper towards the opening which may in dispensing certain dental compositions provide for a reduced extrusion force. Alternatively the passageway may be generally cylindrical which may facilitate manufacturing.

In another embodiment the convexly tapered outer surface of the free end may meet with the inner surface of the passageway at an angle of less than 90 degrees. It has been found that an angle below 90 degrees between the outer surface of the free end and the inner surface of the passageway may provide for a relatively low force required to insert the front of the free end into the entry of the gingival sulcus.

In an embodiment of the invention the method comprises observing an area of the gingiva (for example an area adjacent the entry of the gingival sulcus) for changes in color, and depending on a color change controlling the flow of the dental retraction composition. It has been found that the gingiva tends to change in color, for example turn pale, when it is retracted from the tooth. Therefore a user may stop injecting the dental retraction composition as a certain color change occurs. Thereby the gingival retraction method may be relatively gentle for a patient.

FIG. 1 illustrates a situation at the gingival sulcus adjacent the prepared lateral side of the tooth 10. The cannula 21 has a tapered free end 22 with an opening 23 for dispensing a dental composition. The free end 22 of the cannula 21, because of the taper, has a relatively small diameter at its front end, or front most end, and thus can be placed between the gingiva 12 and the prepared tooth 10. On the other hand because the taper is convex, the free end already has a relatively large diameter adjacent the opening 23. This may allow for displacing the gingiva 12 from the tooth 10 with only slightly inserting the free end 22 between the gingiva 12 and the prepared tooth 10. The free end 22 of the cannula 21 is placed between the gingiva 12 and the prepared tooth 10 so that the gingiva 12 is slightly displaced laterally, away from the tooth 10. This is indicated by a resulting lateral force F2. Because of the shape of the free end 22 of the cannula 21 even in a situation in which the gingival sulcus is located adjacent natural areas of the tooth the gingiva 12 may be exposed to a resulting lateral force F2 oriented to cause the gingival sulcus to open rather than to close. The opening 23 is located in the opened gingival sulcus so that dental composition dispensed from the cannula 21 flows into the gingival sulcus. In fact, it has been found that a shallow insertion of the cannula and therefore moderate mechanical opening of the gingival sulcus by the cannula is sufficient to achieve a relatively good penetration of the dental composition in the gingival sulcus. This is because initial amounts of dental composition injected into the gingival sulcus tend to cause further opening of the gingival sulcus, which again facilitates further injection of dental composition. Thus the invention may allow for properly filling the gingival sulcus with the dental composition, and thereby may provide for a reliable gingival retraction, and proper impressioning of the preparation margin. Because the dental retraction composition is injected into the opened gingival sulcus the gingiva preferably also remain generally uncovered from the dental retraction composition. Therefore areas around the entry of the gingival sulcus preferably remain visible, for example to a dentist. In particular a dentist may observe the color of the gingiva, which tends to turn pale when retracted from the tooth. It has been found that therefore the amount of dental retraction composition dispensed in the gingival sulcus can be relatively well controlled. Thereby the pressure of the dental retraction composition within the gingival sulcus may be kept below limits that would cause the epithelial attachment to be affected. As a result, the risk of detaching the epithelial attachment may be reduced. This is advantageous because tearing the epithelial attachment from the tooth can cause diseases of the gingiva and/or the jaw due to possible penetration of bacteria deeply into the tissue between the tooth and the gingiva.

Furthermore, it has been found that in contrast to known procedures, a lower viscosity dental retraction composition may be used. This is enabled by the invention, for example, because the dental retraction composition is injected within the slightly opened gingival sulcus, rather than being pushed in from outside the gingival sulcus. Therefore, in one embodiment the preferred dental retraction composition has a relatively low viscosity. A lower viscosity dental retraction composition typically allows for example dispensation at lower extrusion forces, which may be more convenient for a user and the patient.

Figure 2:
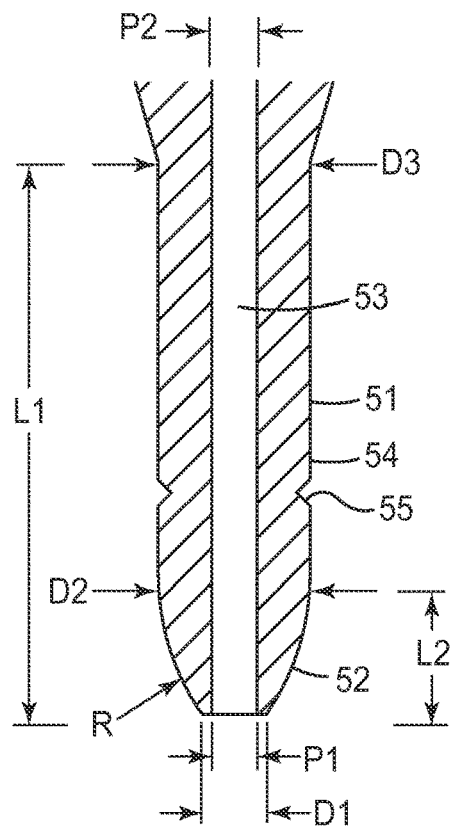
FIG. 2 is a cross-sectional view of a cannula of a container which can be used for storing and dispensing of a dental retraction composition.

FIG. 2 shows a cannula 51 of a container which can be used for storing and dispensing the dental retraction composition. The cannula 51 has a shaft portion 54 and a front or free end 52. The cannula 51 further comprises a passageway 53 having an inner front diameter P1 and an inner rear diameter P2. The passageway 53 may be cylindrical. In this case the inner front and rear diameters P1, P2 are generally equal. In another embodiment the inner front and rear diameters P1, P2 may be different. The passageway 53 may taper from the inner rear diameter P2 toward the inner front diameter P1, in which case P2 is greater than P1. This may for example provide for relatively lower forces required to move a dental composition through the cannula, may even also enable the use of high viscosity compositions although in some instances low viscosity material may be preferred.

The cannula 51 further has a first outer front diameter D1. In the example shown the first outer front diameter D1 is greater than the inner front diameter P1. However in other embodiments the outer front diameter D1 may be the same or approximately the same as the inner front diameter P1. The outer front diameter D1 is preferably measured adjacent the inner front diameter P1. The cannula 51 further has a second outer front diameter D2 and an outer rear diameter D3. Preferably the inner front diameter P1 and/or the outer front diameters D1 form a front end of the free end 52. The free end 52 thus preferably extends between the first and second outer front diameters D1 and D2, or between the inner front diameters P1 and the outer front diameter D2. The shaft portion 54 of the cannula 51 may extend adjacent the free end 52 between the second outer front diameter D2 and the outer rear diameter D3. D2 and D3 may be generally equal, so that the shaft portion 54 is generally cylindrical. Alternatively D2 and D3 may be different, so that the shaft portion 54 is generally conical. For example D3 may be greater than D2, so that the shaft portion 54 tapers from D3 toward D2.

The cannula 51 also has a minimum overall length L1, and the free end 52 has a length L2 with the convex taper tapering along a curve that has an approximate radius R. The dimensions D2, D3, P1, P2, L1, L2 and R may be in within the ranges specified above. P1 and D1 may have equal diameters, however, D1 may be greater than P1 by between 0.05 to 1 mm, in particular by between 0.1 to 0.4 mm. Combinations of the dimensions specified above are possible as appropriate.

The cannula 51 in the example also has a marking 55 for reference with regard to a certain penetration depth of the cannula in the gingival sulcus. The marking 55 is formed as a circumferential notch. However, other embodiments are possible like transitions between colors or surface structures, rims, or lines, and combinations thereof, for example. The marking may help to reduce the risk of injuries of the gingival tissue, and/or help to provide a reliable gingival retraction procedure.

Figure 3:
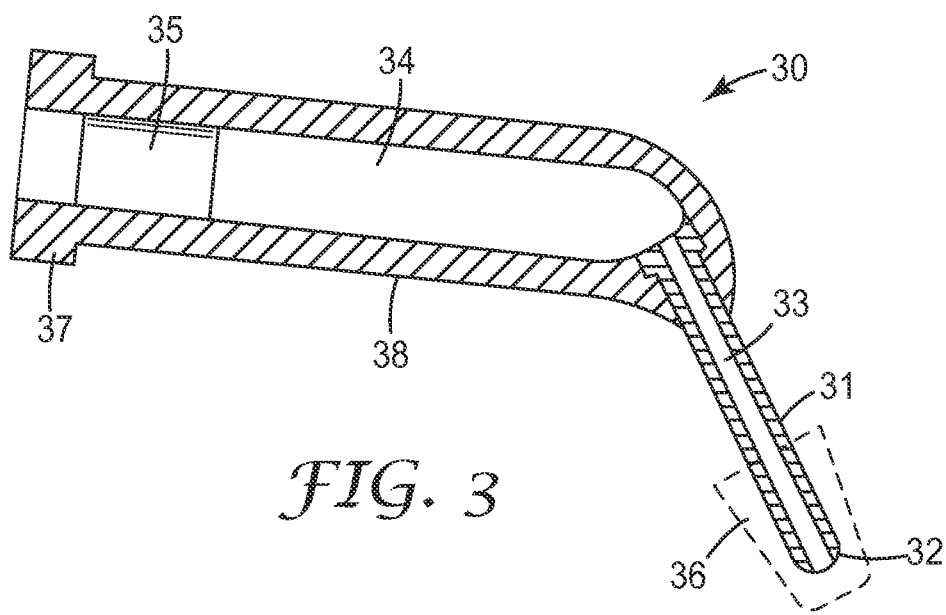
FIG. 3 is a cross-sectional view of a container with cannula and reservoir which can be used for storing and dispensing of an inventive dental retraction composition.

FIG. 3 shows an embodiment of a container 30 which can be used for storing and dispensing of the dental retraction composition. The container 30 has a cannula 31 with a convex tapered free end 32. The container 30 further has a reservoir 34 for holding the dental retraction composition. A piston 35 closes the reservoir and is displaceable therein for extrusion of the dental retraction composition from the reservoir 34. The reservoir 34 opens into a passageway 33 in the cannula 31. A removeable cap 36 (indicated by dashed lines) may be used to close the passageway 33 until the device 30 is used. The container 30 may be used with an applicator device as available under the designation "5706 SD Capsule Dispenser" from 3M ESPE AG, Germany. Therefore, the container 30 has a rim 37 which may be used for engaging the container 30 in the dispenser. The rim 37 may have a notch or flat to lock the container against unintentional rotation during use. Such anti-twist protection may also be otherwise achieved, for example by clamping the container, or by any other positive or frictional fit between the container and the applicator device.

The cannula 31 and the capsule body 38 can be molded from different plastic materials. This allows, for example for selecting a relatively soft plastic material for the cannula 31 so that it can be conveniently used in direct contact with relatively sensitive tissue in a patent's mouth. On the other hand this allows for molding the capsule body 38 from a relatively rigid material which provides sufficient mechanical strength that may be required during extrusion of the dental composition from the device. The cannula 31 and the capsule body 38 may also be molded from different plastic materials. The cannula 31 may be integrally molded with the capsule body 38. This may for example be achieved by injecting a first plastic material into a mold at an end forming the cannula, and generally simultaneously injecting a second plastic material into the mold at an end forming the body. The flow rate of the individual plastic materials may be controlled so that the plastic materials join in an area where the cannula 31 merges with the capsule body 38. Another way to mold the device 30 from two plastic materials includes first molding the cannula 31 and subsequently molding the capsule body 38 onto the pre-molded cannula, or vice versa.

Materials which can be used for producing the cannula 31 include: polyethylene, polypropylene, styrene-butadiene-styrene block copolymer, styrene-butadiene-methacrylate block copolymer, thermoplastic polyurethane. Preferred plastic material for the capsule body 38 include: polyamide, polyoxymethylene, polypropylene, polycarbonate.

Thus, the invention is also directed to a combination of the inventive dental retraction composition and a container for use in retracting gingiva from a human tooth by widening with a the dental retraction composition a gingival sulcus, which is formed between the gingiva and the tooth, the container comprising a cannula with a free end which comprises an opening for dispensing the dental composition, the free end and the opening being shaped so that the opening can be positioned in the entry of the gingival sulcus with an outer lateral surface of the free end touching the tooth and the gingiva, wherein the free end is further shaped so that the gingiva is laterally displaced from the tooth as the cannula is further moved with the opening toward the inside of the gingival sulcus.

Moreover, a further embodiment of the invention is directed to a combination of the inventive dental retraction composition and a container, the container comprising a reservoir and a cannula with a free end which comprises an opening for dispensing the dental retraction composition, wherein the outer lateral surface of the free end extends between a first outer diameter D1 and a second outer diameter D2, the first outer diameter D1 being located adjacent the front end of the free end, and the second outer diameter D2 being located at a distance L2 further to the rear from the first outer diameter D1, wherein D2 is greater than D1.

According to a further embodiment D1 of the device is between about 0.3 mm and about 0.7 mm, D2 is between about 0.7 mm and about 1.3 mm, and L2 is between about 0.3 mm and about 2 mm.

According to a further embodiment the first outer diameter D1 is located adjacent or formed by the opening, the opening having a first inner diameter P1 which is between about 0.3 mm and about 0.7 mm with P1 being equal or smaller than D1.

According to a further embodiment the lateral outer surface of the free end of the device convexly tapers from the second outer diameter D2 toward the first outer diameter D1, and wherein the convex taper in a direction from D2 toward D1 tapers based on a curve that approximates a radius R which is preferably greater than ½ of D2.

According to a further embodiment the cannula further has a length L1 between the first outer diameter D1 and a third outer diameter D3, and a shaft portion extending between the second outer diameter D2 and the third outer diameter D3, wherein the third outer diameter D3 is between about 0.7 mm and about 2 mm with D3 preferably being greater than or about equal to D2, and wherein L1 being between about 6 mm and about 18 mm.

According to a further embodiment the container comprises a reservoir for storing the dental retraction composition, the container being adapted for dispensing the dental retraction composition through the cannula, and further being adapted for comprising a movable piston useful for urging the dental composition towards the cannula.

According to a further embodiment, the cannula extends along a longitudinally axis which is inclined relative to the longitudinal axis of the reservoir by an angle of between about 30 degrees and about 60 degrees, preferably by about 45 degrees.

According to a further embodiment the cannula comprises a passageway between the opening with the first inner diameter P1 and an inlet with a second inner diameter P2, wherein P2 is between about 0.3 and about 1.0 mm with P2 preferably being greater than or equal to P1.

According to a further embodiment the cannula has a marking usable as reference with regard to a penetration depth of the cannula in the gingival sulcus, wherein the marking is formed from at least one of a notch, a rim, a printed line, a transition between colors of outside surfaces of the cannula, and a transition between two surface structures of outside surfaces of the cannula.

According to a particular embodiment, the invention is related to a container as described above, wherein the cannula comprises a first outer diameter D1 of about 0.4 mm, and
a second outer diameter D2 of about 1.0 mm,
wherein the first outer diameter D1 is located adjacent the front end of the free end, and the second outer diameter D2 is located at a distance L2 further to the rear from the first outer diameter D1; and
wherein the distance L2 is preferably about 1.0 mm; and
wherein the first outer diameter D1 is formed by the opening, the opening therefore having a first inner diameter P1 which approximately corresponds to the outer diameter D1; and
wherein the lateral outer surface of the free end convexly tapers from the second outer diameter D2 toward the first outer diameter D1, and wherein the convex taper in a direction from D2 toward D1 tapers based on a curve that approximates a radius R which is preferably about 3.0 mm; and wherein the cannula further has a length L1 between the first outer diameter D1 and a third outer diameter D3, wherein the third outer diameter D3 is about 1.8 mm, and wherein the length L1 is preferably about 11.0 mm; and wherein the container further comprises:

a reservoir for receiving a dental retraction composition, the reservoir being in fluid communication with the cannula;

a piston movable in the reservoir along an extrusion path for advancing the dental retraction composition from the reservoir toward the cannula;

a catch extending laterally to the extrusion path and adapted to catch the device against movement in a direction parallel to the extrusion path; and a resilient adapter, wherein the resilient adapter is laterally resilient relative to the extrusion path; and wherein the device contains the dental retraction composition as described in the text of the present invention.

The invention is also directed to a kit of parts comprising part A and part B, part A comprising the dental retraction composition as described in the text of the invention and part B comprising one or more of the following components: applier, dental impression material, retraction caps, container (especially for storage and dispensing of the inventive composition).

Thus, the kit of parts may comprise besides a dental retraction composition as defined in the text of the present invention a dental impression material.

The impression materials which can be used in combination with retraction devices are not particularly limited in regard to their chemistry and nature. Polyether moieties or silicone moieties containing impression materials have found to be useful.

Examples of polyether moieties containing impression materials are given in U.S. Pat. No. 6,383,279, US 2002/0156149 and US 2005/02503871. Commercially available materials are sold e.g. under the brand Impregum™

Examples of silicone moieties containing impression materials are given in EP 1893163, US 2007/004858 and US 2006/293469. Commercially available materials are sold e.g. under the brand Imprint™ (3M ESPE).

The kit may also comprise retraction caps. Retraction caps can be useful for keeping the retraction material in place until an impression is taken or pushing the dental retraction composition into the sulcus. Retraction caps can be made of soft, tissue friendly material, e.g. cotton. However, other materials might be useful as well. If appropriate a temporary restoration can be used as retraction cap, too. Commercially available retraction caps are e.g. sold under the brand Comprecap™ (CoRene Whaledent).

In some cases compression caps or bridges, temporary crowns or bridges or even a first impression might be used as a kind of accessory during the retraction process. Typically, the dental retraction composition remains in the sulcus for a couple of minutes (e.g. about 1 to about 10 or about 2 to about 6 min to achieve effective mechanical retraction.

The kit may also comprise an applier or capsule dispensers. Those devices are commercially available e.g. from 3M ESPE (cf. Product Catalogue 2007, page 29). Typical appliers have a gear ratio from about 3:1 to about 4:1. A further example of an applier, which can be used, is shown in U.S. Pat. No. 5,362,495, FIG. 3.

The invention is also directed to a process of manufacturing a dental retraction composition as described in the text of the present invention.

The process typically comprises a mixing step.

Thus, the process of manufacturing the dental retraction composition typically comprises the steps of providing the individual components to be mixed and mixing the components.

The invention is also directed to a process of dispensing the dental retraction composition as described in the text of the present invention.

The process typically comprises the following steps:

providing a device or container containing the dental retraction composition as described in the text of the invention, placing the device or container in an applier or dispenser, using the applier or dispenser to dispense the dental retraction composition.

These steps can be repeated, if desired.

Moreover, the invention also features a method of retracting soft tissue from hard dental tissue, comprising the steps of dispensing the dental retraction composition as described in the text of the invention into the sulcus between soft and hard dental tissue, leaving or retaining the dental retraction composition in the sulcus for at least about 10 s or at least about 30 s or at least about 60 s, removing the dental retraction composition from the sulcus and optionally making an impression of the hard dental tissue.

The invention is also directed to the use of a composition as described in the text of the invention for producing a means for retracting soft tissue form hard dental tissue, the means typically comprising a container with a cannula and a reservoir, wherein the composition is stored in the reservoir before use.

According to one embodiment of the invention, the composition is inserted into the sulcus by the aid of the front end of the cannula of the container. This may facilitate the mechanically opening of the sulcus between soft and hard dental tissue.

A typical application procedure can be exemplified as follows:

The dental retraction composition is dispensed by means of an applier out of a nozzle or cannula of a container into the sulcus of a prepared tooth structure of a mammal or human being. The dental retraction composition remains in the sulcus for an appropriate time period, which is typically determined by the practitioner.

After sufficient retraction, the composition is removed from the sulcus using e.g. a dental water air syringe having sufficient pressure. Water-air beam devices are typically included in a dental chair.

The sulcus has been widened due to the application of the inventive dental retraction composition compared to the sulcus before the application. After removal of the composition the shape of the prepared tooth including the preparation margin can be determined, either by an impression-taking process with a common impression material or an by an intra-oral scan of the prepared region using e.g. an inter-oral scanner such as the COS System (chair-side oral scanner) provided by 3M ESPE.

If desired the whole process and workability can also be demonstrated in vitro, e.g. using a Frasaco™ Standard Model AG3 (synthetic tissue surrounding an artificial tooth).

The composition of the present invention does typically not contain components producing a toxic, injurious, or immunological response in living tissue or components or additives which jeopardize the intended purpose to be achieved with the present invention.

Thus, for examples components or additives added in an amount which finally result in a composition, the characteristics of which are in contradiction to the intended purpose of the invention, are usually not contained in the dental retraction composition.

According to a specific embodiment, the inventive dental retraction composition does typically not contain one or more of the following components: fibrillated fibers, starch, cellulose or cellulose derivates and/or water absorbing agents like superabsorbers.

Fibrillated fibers are e.g. natural fibres based on cellulose or man-made fibres e.g. polyester, polyamide or fibres of glass. It was found that the addition of fibers can sometimes be detrimental to the whole retraction process in that the fiber structure in the paste might decrease the storage modulus, compared to pastes without fibers.

The complete disclosures of the patents, patent documents, and publications cited herein are incorporated by reference in their entirety as if each were individually incorporated. Various modifications and alterations to this invention will become apparent to those skilled in the art without departing from the scope and spirit of this invention. The above specification, examples and data provide a description of the manufacture and use of the compositions and methods of the invention. The invention is not limited to the embodiments disclosed herein. One skilled in the art will appreciate that many alternative embodiments of the invention can be made without departing from the spirit and scope of thereof.

The following examples are given to illustrate, but not limit, the scope of this invention. Unless otherwise indicated, all parts and percentages are by weight.

EXAMPLES

Unless otherwise indicated, all parts and percentages are on a weight basis, all water is deionized water, and all molecular weights are weight average molecular weight. Moreover, unless otherwise indicated all Experiments were conducted at ambient conditions (23° C.; 1013 mbar).

Measurements

Storage Modulus:

The storage modulus was measured using a Physica Rheometer (Paar MCR 300) with plate/plate geometry (diameter of plates: 15 mm; knurled surface). The initial gap was set to 1 mm and is force-operated during the measurement to (1+/−1)N. The oscillating measurement was performed using a linear ramp from 1 to 10 $s^{-1}$ radial frequency during 300 s. The deflection was set to 0.01%. The storage modulus was determined at 5 $s^{-1}$ radial frequency at room temperature (23° C.).

Extrusion Force:

The extrusion force was measured using as testing device a Zwick Z020 machine (Zwick Roell Comp.). The testing device was equipped with a holder for containers and a small stamp to press against the piston inserted in the container and sealing the reservoir. The dimensions of the stamp corresponded to those used in commercially available single container dispensers (commercially available e.g. from 3M ESPE Comp.; order code 5706 SD). The feeding speed was set to 1.0 mm/s. The force was measured after the initial yield point was overcome (about 6-9 mm from starting point). The extrusion force was determined as an average value out of six individual measurements. The geometry of the cannula of the container is given in FIG. 4, the geometry of the piston inserted in the container is shown in FIGS. 5 and 6.

Figure 7:
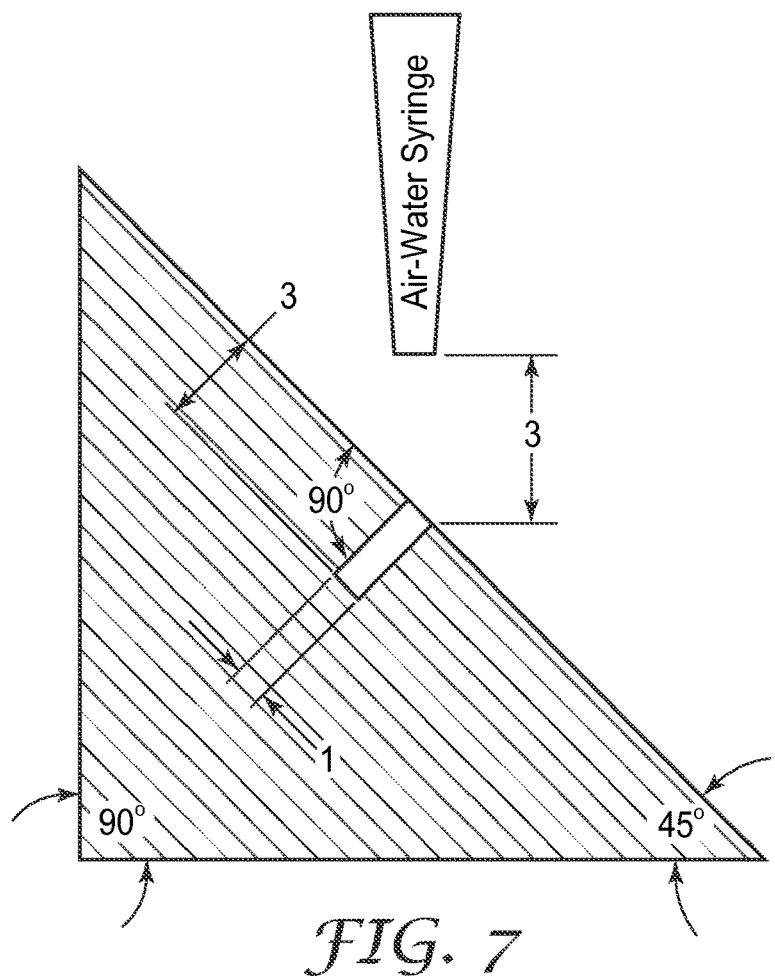
FIGS. 7 and 8 show the device which was used for measuring the rinsing time.
Figure 8:
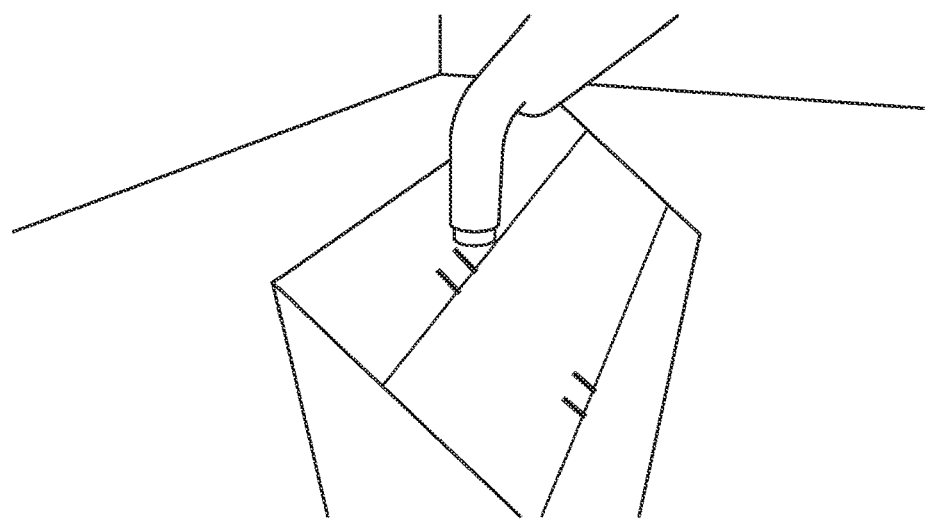

Rinsing Time:

The rinsing time was measured using a dental treatment unit (KaVo ESTETICA™ Sensus 1066; KaVo Comp.). A polymer block made out of polyoxymethylene was cut into a triangle form having a 45° surface towards the rinsing direction. A 1 mm wide and 3 mm deep ditch was milled in right angle towards the surface into the block (see FIGS. 7 and 8). The 3-way handpiece syringe of the dental treatment unit was fixed in a distance of 5 mm (water-/air outlet) to the block and perpendicular to the subsurface of the bottom. The dry ditch was filled with a 5 mm string of paste and the surface and sides were smoothened. The black lines in FIG. 8 mark the region of the ditch which was filled with paste. The paste was rinsed out of the ditch by moving the block manually into longitudinal direction until all the paste was rinsed of. The air-pressure used was 475 kPa and the water pressure 250 kPa. The rinsing time was determined as an average out of two individual measurements.

The components used are listed in Table 1.

TABLE 1

| Description | Descriptive Name | Availability |
| --- | --- | --- |
| layer type 1:1 silicate mineral | Kaolin TecFK | Quartz Werke; Frechen |
| layer type 1:2 silicate mineral | Mica SFG70 | Quartz Werke; Frechen |
| astringent | $AlCl_3 * 6H_2O$ | Aldrich, Fluka |
| Polydimethylsiloxane, trimethylsiloxy terminated, CASNR: 63148-62-9, (viscosity 1-10 cSt) | Silicon oil | Aber, Wacker |
| lemon oil; | Article No. 2049 | Vögele; Lauffen |
| retraction paste | Expasyl™ | Acteon |

Synthesis of Dental Retraction Composition

The individual components were placed in a speedmixer and mixed for about 60 s at about 2,400 rpm. The mixing process was started immediately after bringing the components in contact. The mixing step was repeated if the obtained paste was cloddy.

Alternatively the composition can be mixed in a 3-finger-kneader.

The compositions described in Table 2 below were prepared as described above and analysed with respect to rinsing time, storage modulus and extrusion force.

TABLE 2

| # | Composition [wt.-%] | content kaolin[1] | content mica[2] | Extrusion Force [N] | Rinsing Time [s] | Storage Modulus [kPa] |
| --- | --- | --- | --- | --- | --- | --- |
| 1 | Expasyl (Acteon, Lot#: 4813) | | | 185 | 11 | 8100 |
| 2 | Expasyl: (Acteon, Lot#: 1066) | | | 259 | 13 | 8000 |

TABLE 2-continued

| # | Composition [wt.-%] | content kaolin[1] | content mica[2] | Extrusion Force [N] | Rinsing Time [s] | Storage Modulus [kPa] |
|---|---|---|---|---|---|---|
| 3 | US 2008/0220050 (Example 1) | 0 | 0 | No paste like structure | No paste like structure | No paste like structure |
| 4 | US2008/0220050 (Example 3) | 0 | 0 | No paste like structure | No paste like structure | No paste like structure |
| 5 | US2008/0220050 (Example 5) | 0 | 0 | No paste like structure | No paste like structure | No paste like structure |
| 6 | Kaolin: 65<br>$AlCl_3*6H_2O$: 15<br>$H_2O$: 20 | 100 | 0 | 130 | 11 | 7742 |
| 7 | Kaolin: 32.5<br>Mica: 32.5<br>$AlCl_3*6H_2O$: 15<br>$H_2O$: 20 | 50 | 50 | 142 | 10 | 7626 |
| 8 | Kaolin: 8.81<br>Mica: 58.96<br>$AlCl_3*6H_2O$: 15<br>$H_2O$: 16.20<br>Silicon oil: 1<br>Pigment: 0.03 | 13 | 87 | 141 | 6 | 4017 |
| 9 | Kaolin: 4.875<br>Mica: 60.125<br>$AlCl_3*6H_2O$: 15<br>$H_2O$: 20 | 7.5 | 92.5 | 148 | 6 | 3529 |
| 10 | Kaolin: 3.36<br>Mica: 63.81<br>$AlCl_3*6H_2O$: 15<br>$H_2O$: 15.8<br>Silicon oil: 2<br>Pigment: 0.03 | 5 | 95 | 125 | 6 | 4212 |
| 11 | Mica: 65<br>$AlCl_3*6H_2O$: 15<br>$H_2O$: 20 | 0 | 100 | 124 | 5 | 897 |

[1],[2] with respect to the whole content of silica mineral.

Figure 9:
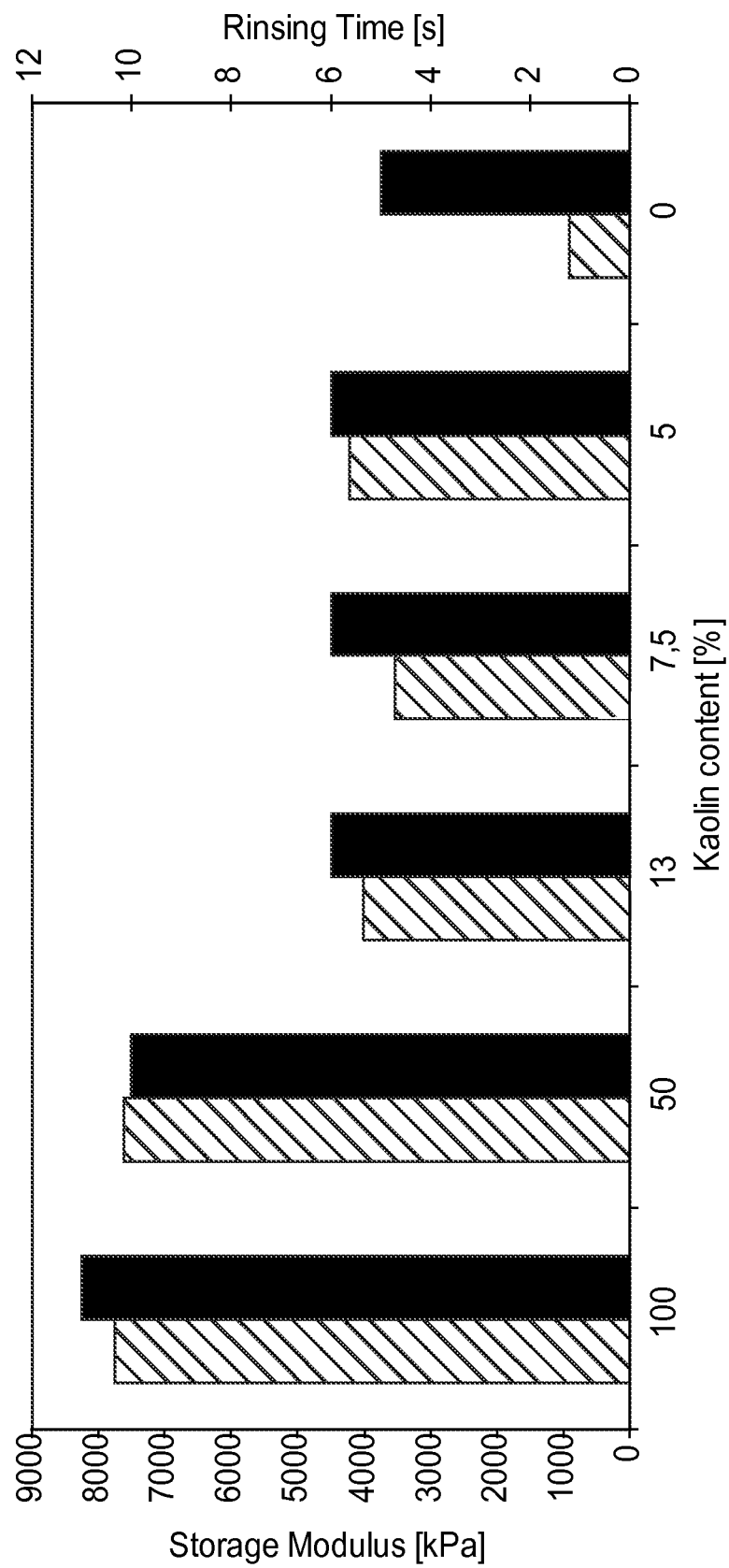
FIG. 9 shows a diagram comparing storage modulus and rinsing time for various compositions.

FIG. 9 shows the above results with respect to storage modulus and rinsing time in a diagram. If the content of Kaolin is too low, a sufficient storage modulus cannot be obtained. If, on the other hand, the content of Kaolin is too high, the rinsing time is too long.

The invention claimed is:

1. A dental retraction composition comprising:
    a liquid in an amount from 10 wt.-% to 35 wt.-% with respect to the whole composition;
    a layer type 1:1 silicate mineral in an amount from 1 wt. % to 30 wt.-% with respect to the whole composition and a layer type 2:1 silicate mineral in an amount from 35 wt.-% to 70 wt.-% with respect to the whole composition;
    an astringent in an amount from 0.01 to 30 wt.-% with respect to the whole composition; and
    additive(s) in an amount from 0 to 30 wt.-% with respect to the whole composition,
    wherein the dental retraction composition does not contain starch.

2. The dental retraction composition according to claim 1, wherein the layer type 1:1 silicate mineral is selected from the group consisting of kaolinite, lizardite, halloysite and mixtures and combinations thereof.

3. The dental retraction composition according to claim 1, wherein the layer type 2:1 silicate mineral is selected from the group consisting of talc-pyrophyllite type minerals, smectite type minerals, vermiculite type minerals, illites type minerals, mica type minerals and mixtures and combinations thereof.

4. The dental retraction composition according to claim 1, wherein the liquid is selected from the group consisting of water, alcohols, ketones, glycerine, glycols, silicone oils and mixtures and combinations thereof.

5. The dental retraction composition according to claim 1 comprising one or more additives selected from the group consisting of colorants, anti-microbial agents, anti-evaporation agents, flavouring agents, surfactants, preserving agents, rheology modifiers, pH buffering agents and mixtures and combinations thereof.

6. The dental retraction composition according to claim 1 being essentially free of one or more of the following components: fibrillated fibers, cellulose and substances swellable with water.

7. The dental retraction composition of claim 1 wherein the storage modulus of the dental retraction composition is at least about 3000 kPa.

8. A method for retracting soft dental tissue from hard dental tissue comprising:
    providing a dental retraction composition comprising: a liquid in an amount from 10 wt.-% to 35 wt.-% with respect to the whole composition; a layer type 1:1 silicate mineral in an amount from 1 wt. % to 30 to 30 wt.-% with respect to the whole composition and a layer type 2:1 silicate mineral in an amount from 35 wt.-% to 70 wt.-% with respect to the whole composition; an astringent in an amount from 0.01 wt.-% to 30 wt.-% with respect to the whole composition, and additive(s) in an amount from 0 wt.-% to 30 wt.-% with respect to the whole composition; wherein the dental retraction composition does not contain starch; wherein said dental retraction composition is contained in a container comprising a reservoir and a cannula; and
    applying said dental retraction composition to a sulcus between soft and hard dental tissue.

9. The method according to claim 8, further comprising: retaining the dental retraction composition in the sulcus for at least about 5 seconds, and removing the dental retraction composition from the sulcus.

10. The method according to claim 8, wherein the step of applying includes dispensing the dental retraction composition from the container into the sulcus.

11. A process of dispensing a dental retraction composition, the process comprising:
providing a dental retraction composition contained in a container comprising a reservoir and a cannula, wherein the dental composition comprising: a liquid in an amount from 10 wt.-% to 35 wt.-% with respect to the whole composition; a layer type 1:1 silicate mineral in an amount from 1 wt. % to 30 to 30 wt.-% with respect to the whole composition and a layer type 2:1 silicate mineral in an amount from 35 wt.-% to 70 wt.-% with respect to the whole composition; an astringent in an amount from 0.01 wt.-% to 30 wt.-% with respect to the whole composition, and additive(s) in an amount from 0 wt.-% to 30 wt.-% with respect to the whole composition; wherein the dental retraction composition does not contain starch:
placing the container in an applier, and
using the applier for dispensing the dental retraction composition out of the container.

12. A dental retraction composition comprising:
a liquid in an amount from 10 wt.-% to 35 wt.-% with respect to the whole composition;
a layer type 1:1 silicate mineral in an amount from 1 wt. % to 30 wt.-% with respect to the whole composition and a layer type 2:1 silicate mineral in an amount from 35 wt.-% to 70 wt.-% with respect to the whole composition;
an astringent in an amount from 0.01 to 30 wt.-% with respect to the whole composition; and
additive(s) in an amount from 0 to 30 wt-% with respect to the whole composition, wherein the storage modulus of the dental retraction composition is at least about 3000 kPa.

* * * * *

UNITED STATES PATENT AND TRADEMARK OFFICE
CERTIFICATE OF CORRECTION

PATENT NO. : 10,548,819 B2
APPLICATION NO. : 13/375038
DATED : February 4, 2020
INVENTOR(S) : Andreas Maurer et al.

Page 1 of 2

It is certified that error appears in the above-identified patent and that said Letters Patent is hereby corrected as shown below:

On the Title Page

Column 2 (item (74) Attorney, Agent, or Firm)
Line 2, delete "Compa" and insert -- Company --, therefor.

Column 2 (item (57) Abstract)
Line 3, after "comprising" delete "liquid".

In the Specification

Column 2
Line 15 (approx.), delete "astringent" and insert -- astringent. --, therefor.

Column 8
Line 38, delete "kPa" and insert -- kPa. --, therefor.

Column 9
Line 19, delete "ellag" and insert -- ellagic --, therefor.

Column 10
Line 2, delete "chromophtalblue" and insert -- cromophtal blue --, therefor.

Column 10
Line 3, delete "Neazopon" and insert -- Neozapon --, therefor.

Column 10
Line 24, delete "propylhexidrin," and insert -- propylhexedrine, --, therefor.

Signed and Sealed this
Twenty-fifth Day of August, 2020

Andrei Iancu
*Director of the United States Patent and Trademark Office*

Column 10
Lines 24-25, delete "adrenochrom-monose" and insert -- adrenochrome-monose --, therefor.

Column 10
Line 25, delete "propylgallat," and insert -- propylgallate, --, therefor.

Column 17
Line 44 (approx.), delete "a the" and insert -- a --, therefor.

Column 19
Line 51, delete "(CoRene" and insert -- (Coltène --, therefor.

Column 20
Line 56, after "or" delete -- an --.

Column 22 (Table 1)
Line 44 (approx.), delete "ExpasylTM" and insert -- Expasyl™ --, therefor.

In the Claims

Column 25
Line 15, in Claim 11, delete "to 30 to 30" and insert -- to 30 --, therefor.

Column 26
Line 2, in Claim 11, delete "starch:" and insert -- starch; --, therefor.

Column 26
Line 17 (approx.), in Claim 12, delete "wt-%" and insert -- wt.-% --, therefor.